(12) United States Patent
Alcade et al.

(10) Patent No.: US 7,041,679 B2
(45) Date of Patent: *May 9, 2006

(54) CRYSTALLINE FORMS OF OSANETANT

(75) Inventors: Alain Alcade, Toulouse (FR); Gilles Anne-Archard, Toulouse (FR); Patrick Gros-Claude, Toulouse (FR); Olivier Monnier, Villeveyrac (FR); Jérome Roche, Prades le Lez (FR)

(73) Assignee: sanofi-aventis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/651,313

(22) Filed: Aug. 28, 2003

(65) Prior Publication Data

US 2004/0044215 A1  Mar. 4, 2004

Related U.S. Application Data

(63) Continuation of application No. 09/762,020, filed as application No. PCT/FR99/01914 on Aug. 3, 1999, now abandoned.

(30) Foreign Application Priority Data

Aug. 5, 1998 (FR) .................................. 98 10107

(51) Int. Cl.
*A61K 31/4545* (2006.01)
*C07D 401/06* (2006.01)

(52) U.S. Cl. ...................... 514/316; 514/318; 546/187; 546/188; 546/189

(58) Field of Classification Search ................ 514/316, 514/318; 546/187, 188, 189
See application file for complete search history.

(56) References Cited

U.S. PATENT DOCUMENTS

| 5,741,910 A | 4/1998 | Bichon et al. ............... 514/329 |
| 5,942,523 A | 8/1999 | Bichon et al. ............... 514/316 |
| 6,040,316 A * | 3/2000 | Chen et al. .................. 514/316 |
| 6,124,316 A * | 9/2000 | Bichon ........................ 514/316 |

FOREIGN PATENT DOCUMENTS

| EP | 0 673 928 | 9/1995 |
| WO | WO 98/05640 | 2/1998 |

OTHER PUBLICATIONS

Rouhi "The right stuff" Chem. Eng. News, p. 32-35, Feb. 24, (2003).*
Brittain "Polymorphism in pharmaceutical solids" Marcel Dekker, p. 331-333 (1999).*
Rowland et al. "Clinical pharmacokinetics" p. 123 (1995).*
Chen, Huai. G. et al., Bioorg. Med. Chem. Lett., (1997), vol. 7, No. 5, pp. 555-560.
Giardina, G.A.M. et al., Bioorg. Med. Chem. Lett., (1996), vol. 6, No. 19, pp. 2307-2310.

* cited by examiner

Primary Examiner—Celia Chang
(74) Attorney, Agent, or Firm—Balaram Gupta

(57) ABSTRACT

The invention relates to crystalline forms of (R)-(+)-N-[[3-[1-benzoyl-3-(3,4-dichlorophenyl)piperidin-3-yl]prop-1-yl]-4-phenylpiperidin-4-yl]-N-methylacetamide and to processes for preparing them.

18 Claims, 2 Drawing Sheets

CRYSTALLINE FORMS OF OSANETANT

CROSS REFERENCE TO RELATED APPLICATIONS

Figure 1:
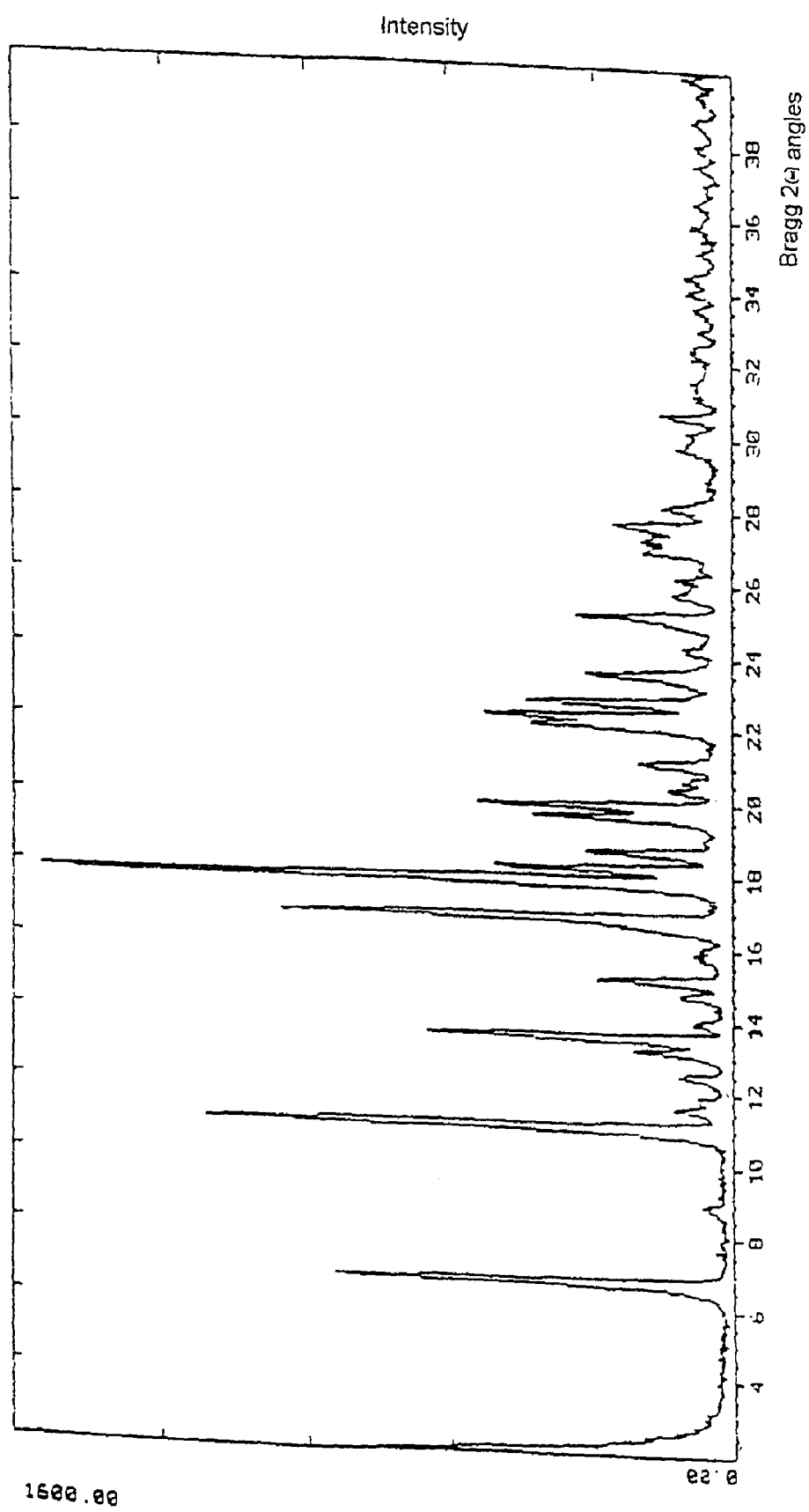

This application is a continuation of prior application Ser. No. 09/762,020 filed Mar. 8, 2001 now abandoned, which in turn is a 35 U.S.C. §371 application of PCT International application No. PCT/FR99/01914, filed Aug. 3, 1999, which in turn claims priority from French application No. 98/10107 filed Aug. 5, 1998.

The present invention relates to two different crystalline forms of (R)-(+)-N-[[3-[1-benzoyl-3-(3,4-dichlorophenyl)piperidin-3-yl]prop-1-yl]-4-phenylpiperidin-4-yl]-N-methylacetamide and to a process for their preparation. (R)-(+)-N-[[3-[1-Benzoyl-3-(3,4-dichlorophenyl)piperidin-3-yl]prop-1-yl]-4-phenylpiperidin-4-yl]-N-methylacetamide, hereinafter denoted by its International Non-proprietary Name "osanetant", is the first antagonist of the NK-3 receptor described in the literature, the preparation of which, in particular in the hydrochloride form, is illustrated in EP-A-673 928.

According to this document, osanetant is prepared by reacting N-methyl-N-(4-phenylpiperidin-4-yl)acetamide with 1-benzoyl-3-(3,4-dichlorophenyl)-3-(methanesulfonyloxyprop-1-yl)piperidine and by converting the osanetant thus obtained to its hydrochloride. It has been found that osanetant hydrochloride is isolated in the form of an amorphous solid which is difficult to purify. This product comprises impurities originating from the preceding synthetic stages.

Preparative chromatography starting from osanetant base can be used to obtain osenetant in the pure form.

Furthermore, it has been found that by isolating osanetant in the benzenesulfonate form, for example in the form of the solvate of its benzenesulfonate with 4-methyl-2-pentanone, an extremely pure product is obtained which readily gives chemically pure osanetant.

It has also been found that by suitably crystallizing osanetant, two different crystalline forms are obtained. The starting osanetant is preferably chemically pure. The term "chemically pure" is understood to mean that the osanetant comprises less than 20% of impurities and preferably less than 10%.

More particularly, a process for the crystallization of osanetant has been found, characterized in that:

i) osanetant is crystallized from an ethanol/water mixture or from isopropanol to give crystalline form I;

ii) osanetant is crystallized from an ethanol/isopropyl ether/water mixture to give crystalline form II.

Preferably, according to the present invention, the osanetant to be crystallized is prepared by neutralization of its benzenesulfonate.

Thus, according to one of its aspects, the present invention relates to a process for the preparation of osanetant, characterized in that osanetant benzenesulfonate is prepared and then it is neutralized with a base.

Osanetant benzenesulfonate can be obtained from an osanetant salt. Thus, according to the process of the present invention:

a) an osanetant salt is neutralized with a base and subsequently the osanetant solution thus obtained is treated with benzenesulfonic acid;

b) the osanetant benzenesulfonate thus obtained is neutralized with a base.

This process is applied in particular to the preparation of pure osanetant from osanetant hydrochloride. Thus, according to a specific aspect of the process of the present invention:

a) osanetant hydrochloride is neutralized with a base and, subsequently, the osanetant solution thus obtained is treated with benzenesulfonic acid; and (b) the benzenesulfonate is neutralized with a base;

and then the pure osanetant thus obtained is isolated.

In stage (a), osanetant hydrochloride is treated with a base, such as sodium hydroxide, potassium hydroxide or ammonia in water, in the presence of a solvent, preferably 4-methyl-2-pentanone, and then the osanetant is advantageously isolated in the benzenesulfonate form by treating the osanetant solution thus obtained with benzenesulfonic acid, which makes it possible to obtain an extremely pure product. As the salification is generally carried out in 4-methyl-2-pentanone and as this solvent has a tendency to give solvates, the osanetant benzenesulfonate may be in the form of a solvate with 4-methyl-2-pentanone, preferably with 0.25 mol of the latter. The yields are virtually quantitative, generally greater than 94%.

In stage (b), the osanetant benzenesulfonate or, in the case where, in stage a), 4-methyl-2-pentanone is used as solvent, its solvate with 4-methyl-2-pentanone is neutralized with a base, such as sodium hydroxide, potassium hydroxide or ammonia, and the osanetant is isolated, generally from its solutions in an alcohol, preferably ethanol or isopropanol, optionally as a mixture with other solvents, from which the osanetant crystallizes.

The neutralization of stage b) is generally carried out in a halogenated solvent, such as dichloromethane, 1,2-dichloroethane or 1,1,1-trichloroethane, as a mixture with water. The neutralization can also be carried out in an ethanol-water mixture in order to directly obtain osanetant in crystalline form I.

According to another of its aspects, the present invention relates to a process for the crystallization of osanetant, characterized in that:

either water is added to a solution of osanetant in ethanol and heating is carried out to a temperature of less than or equal to the reflux temperature of the solvent, preferably 60 to 75° C., and then cooling is carried out in order to obtain osanetant-crystalline form I;

or a solution of osanetant in isopropanol is heated to a temperature of less than or equal to the reflux temperature of the solvent, preferably 60 to 75° C., and cooling is carried out in order to obtain osanetant-crystalline form I;

or isopropyl ether and water are added to a solution of osanetant in ethanol, heating is carried out, preferably to reflux of the solvent, and cooling is carried out in order to obtain osanetant-crystalline form II.

In the crystallization process of the invention, use may be made of pure osanetant obtained by any process. Use is advantageously made of osanetant obtained by the preparation process described above.

Thus, for example, when the neutralization of the osanetant benzenesulfonate according to stage (b) of the above process is completed, the osanetant can be, dissolved in ethanol or isopropanol and can be isolated either in its crystalline form I or in its crystalline form II.

According to an alternative embodiment of the crystallization process of the invention, it is possible, in order to isolate the crystalline form I, to add water to the ethanolic solution comprising the osanetant, for example in a proportion of 40% water and 60% ethanol; then to heat to 60–75°

C. and to allow to cool with vigorous stirring to 20–25° C. Osanetant-crystalline form I crystallizes and the crystallization can advantageously be accelerated by seeding with crystals of osanetant-crystalline form I; the temperature is then increased to 45–50° C., slow cooling to 0° C. is carried out and this temperature is maintained until the crystallization is complete. Osanetant-crystalline form I is then isolated by filtration, washed and dried.

According to an alternative, it is possible, in order to isolate the crystalline form I, to add water to the ethanolic solution comprising the osanetant, heated to 60–75° C. and to allow to slowly cool with vigorous stirring to a temperature in the region of 40° C.; to seed the medium with crystals of osanetant-crystalline form I, to continue to slowly cool to 20–25° C. and to maintain at this temperature for a few hours; to subsequently slowly reheat the osanetant suspension formed to 45–50° C., to maintain at this temperature for a few hours, then to slowly cool to 20° C. and, finally, to filter off the crystals formed.

According to another alternative embodiment of the crystallization process of the invention, it is also possible, in order to isolate the crystalline form I, to heat an isopropanolic solution of osanetant to 60–80° C., preferably 60–75° C., and then to cool it with stirring, preferably with a cooling gradient, to 0° C. The osanetant-form I is then isolated by filtration, washed and dried.

Advantageously, the isopropanolic osanetant solution is cooled to a temperature of between 0° C. and 50° C., preferably 35–50° C., the crystallization is then initiated by seeding and, if appropriate, cooling is continued to 0° C. and then this temperature is maintained until the crystallization is complete.

The concentration of the onasetant in the isopropanol is preferably between 200 g and 350 g/liter, more particularly between 250 g and 300 g/liter.

When the crystallization is carried out in a reaction volume of 0.5 liter to 2 liters, stirring is preferably carried out with rates of between 200 and 600 revolutions/minute. It is possible, for example, to use, as stirrer, an impeller-type paddle stirrer.

In order to carry out a controlled cooling, use is preferably made of a linear cooling gradient of −10 to −30° C./hour, for example of −20° C./hour.

In order to isolate the crystalline form II, it is advantageously possible to add isopropyl ether to the ethanolic solution comprising the osanetant, then to heat to reflux and subsequently to add isopropyl ether and 0.5 to 3% of water. By cooling to 40–50° C., the crystalline form II of osanetant crystallizes; the suspension is preferably cooled to 25° C. and the crystalline form II is isolated by filtration, washing and drying.

When the two crystalline forms of osanetant are obtained from ethanolic solutions of the product, it is possible to easily change from one crystalline form to the other by heating at reflux in ethanol/water or ethanol/isopropyl ether/water mixtures under the conditions indicated above.

More particularly, it is possible to change from osanetant-crystalline form I to osanetant-crystalline form II by heating a mixture of crystalline form I to reflux in an approximately 1/1 (v/v) mixture of ethanol/isopropyl ether, by adding water and isopropyl ether and by cooling as described above. Likewise, it is possible to change from osanetant-crystalline form II to osanetant-crystalline form I by heating the crystalline form II to reflux in an approximately 1/1 (v/v) ethanol/water mixture and by cooling as described above.

In all cases, it is preferable to filter the hot solutions, before cooling, in order to remove interfering crystallization seeds which may be present.

Thus, according to an advantageous procedure, the process for the preparation of osanetant according to the present invention is characterized in that stage (a) is carried out as illustrated above, then (b) the osanetant benzenesulfonate thus obtained or a solvate of the latter with 4-methyl-2-pentanone is neutralized with an alkaline hydroxide in a halogenated solvent chosen from dichloromethane, 1,2-dichloroethane or 1,1,1-trichloroethane, and either ethanol is added, the halogenated solvent is distilled off by azeotropic distillation and water is added to the ethanolic solution comprising the osanetant at a temperature of 60 to 75° C. and the osanetant-crystalline form I is allowed to crystallize;

or isopropanol is added, the halogenated solvent is distilled off by azeotropic distillation, heating is then carried out to a temperature of 60–80° C. and the osanetant-crystalline form I is allowed to crystallize;

or ethanol is added, the halogenated solvent is distilled off by azeotropic distillation and isopropyl ether and water are added to the ethanolic solution of the osanetant, heating is then carried out to reflux and the osanetant-crystalline form II is allowed to crystallize.

According to a specific aspect of the present invention, the osanetant-crystalline form I is prepared by the process which comprises the stages which consist in heating an ethanolic solution of osanetant to 60–75° C., in adding water, in cooling to 20–25° C., in then either initiating the crystallization or waiting for the first crystals to appear and, subsequently, in increasing the temperature to 45–50° C., in cooling to to 0° C. and in maintaining this temperature until the crystallization is complete.

According to a preferred aspect of the present invention, the osanetant-form I can be obtained by using the process which comprises the stages which consist in:

heating to between 60 and 75° C. a solution of osanetant in isopropanol at a concentration of 200–350 g/l, preferably 250–300 g/l;

cooling the solution to a temperature of between 0° and 50° C., for example 35–50° C., preferably 40° C., with a linear cooling gradient of −10° C. to −30° C., preferably −20° C./hour, with stirring;

seeding the medium with 2 to 10%, preferably 5%, of osanetant-form I;

cooling the medium to 0° C. with a linear cooling gradient of −10° C. to −30° C./hour, preferably −20° C./hour, and in maintaining at this temperature until the crystallization [lacuna] complete;

isolating the crystals formed.

The application of the operating conditions according to the preferred process of the present invention makes it possible to obtain a crystallization yield for osanetant-form I of greater than 90% in a time of less than 10 hours.

According to another specific aspect of the present invention, the osanetant-crystalline form II is prepared by a process which comprises the stages which consist in heating to reflux a solution of osanetant in an approximately 1/1 (v/v) ethanol/isopropyl ether mixture, in adding isopropyl ether approximately and water (proportions with respect to the final volume: isopropyl ether approximately 3.33 and water 0.02 to 0.05), in first allowing to cool to 40–50° C., for example approximately 45° C., and then initiating the crystallization or waiting for the first crystals to appear and subsequently cooling to 20–25° C. until the crystallization is complete.

According to another of its aspects, a subject matter of the present invention is osanetant-crystalline form I and osanetant-crystalline form II capable of being obtained by the process illustrated above, in particular by stages (a) and (b), and by the process of crystallization from an osanetant solution.

More particularly, according to this aspect, the present invention relates to:

osanetant-crystalline form I capable of being obtained:
1) by the process comprising the stages which consist in heating to 60–75° C. an ethanolic osanetant solution, in adding water, in cooling to 20–25° C., in then either initiating the crystallization or waiting for the first crystals to appear and in subsequently increasing the temperature up to 45–50° C., in cooling to 0° C. and this temperature is maintained until the crystallization is complete;
2) or by the process comprising the stages which consist in heating to 60–80° C. a solution of osanetant in isopropanol, in cooling to a temperature of between 0° C. and 5° C., preferably 35–50° C., in then initiating the crystallization, in cooling to 0° C. and maintaining at 0° C. until the crystallization is complete;

osanetant-crystalline form II capable of being obtained by the process comprising the stages which consist in heating to reflux a mixture of osanetant and of approximately 1/1 (v/v) ethanol/isopropyl ether, in adding isopropyl ether and water in proportions with respect to the final volume of: isopropyl ether approximately 3.33 and water 0.02 to 0.05 (v/v), in allowing to cool first to 40–50° C., and then either initiating the crystallization or waiting for the crystals to appear, in subsequently cooling to ambient temperature (20–25° C.) and in maintaining at this temperature until the crystallization is complete.

The essential characteristics of the novel crystalline forms of osanetant were determined by differential scanning calorimetry (DSC), which gives, by thermograms obtained with a Perkin-Elmer calorimeter, the melting temperature and the enthalpy related to said melting.

The DSC was carried out using a Perkin-Elmer DSC 7 device which is calibrated with respect to the melting endotherms of indium and of lead or of cyclohexane. For this analysis, from 3 to 6 mg of product were used in an aluminum dish with a crimped and pierced cap, in a temperature region from 50° C. to 180° C., at a heating rate of 10° C./minute, using nitrogen as flushing gas.

Generally, in the present description, the physical constants were determined using samples of the forms I and II with purities of greater than or equal to 99.9%.

The melting temperature and the enthalpy of fusion constitute essential characteristics in identifying each crystalline form.

Said forms can also be characterized by powder X-ray diffractometry. The powder X-ray diffraction profile (diffraction angles) was determined with a Siemens D 500 TT diffractometer with a 40 kV generator, rear monochromator, Cu K$\alpha$1 ($\lambda$=1.5406 Å), silicon support, and in a scanning range from 4° to 40° at 1° per minute in Bragg 2$\theta$.

The crystalline form I of osanetant, which exhibits:
a melting temperature with a peak with a maximum at 143.6° C.±0.5° C.
an enthalpy of fusion of 68.5±0.5 J/g, constitutes a preferred aspect of the present invention.

Osanetant-crystalline form I was also analyzed by powder X-ray diffraction. The qualitative study of the diffractograms made it possible to determine that this crystalline form exhibits characteristic Bragg 2$\theta$ lines at approximately 17.81°, 11.04° and 16.84°.

The crystalline form II of osanetant, which exhibits:
a melting temperature of 141.8±0.5° C.
an enthalpy of fusion of 65.0±0.5 J/g, constitutes another preferred aspect of the present invention.

Osanetant-crystalline form II was also analyzed by powder X-ray diffraction. The qualitative study of the diffractograms made it possible to determine that this crystalline form exhibits characteristic Bragg 2$\theta$ lines at at approximately 18.35°, 18.58° and 18.97°.

The fact of controlling the reproducibility of the process for the manufacture of each of the crystalline forms of osanetant makes it possible to have available well defined crystalline forms and is thus very advantageous for the use of osanetant as medicament and for the acquisition of the authorizations necessary for the marketing of said medicament.

More particularly, the production of a product having a well defined crystalline form makes it possible to prepare pharmaceutical formulations having a constant and reproducible composition, which is particularly advantageous when said formulations are intended for oral administration.

Thus, according to another of its aspects, a subject matter of the present invention is a pharmaceutical composition comprising, as active principle, osanetant-crystalline form I or osanetant-crystalline form II.

The crystalline forms of the invention can be appropriately administered orally, parenterally, sublingually, transdermally or by inhalation. The amount of active principle to be administered depends on the nature and on the seriousness of the diseases to be treated and on the weight of the patients. Nevertheless, the active principle, administered in a dosage unit, is present in said dosage unit in an amount of 0.5 to 500 mg, advantageously of 1 to 250 mg, preferably of 2 to 100 mg. This dosage unit can be administered one to four times daily, preferably one or two times daily.

In the single-dose forms of the pharmaceutical compositions of the present invention, the active principle is preferably mixed with pharmaceutical excipients and it is administered to animals and to human beings for the treatment of diseases which require a treatment based on the administration of an antagonist of the NK-3 receptors, such as, for example, those indicated in EP-A-673 928 (for example diseases associated with a dysfunction of the dopaminergic systems such as schizophrenia. Parkinson's disease, diseases associated with a dysfunction of the dopaminergic system such as anxiety, vigilance disorders as well as epileptic diseases of any form and in particular Grand Mal, dementia, neurodegenerative diseases, and peripheral diseases in which the participation of the central nervous system and/or the peripheral nervous system occurs via neurokinin B acting as central neurotransmitter or neuromodulator, such as pain, migraine, acute or chronic inflammation, cardiovascular disorders, in particular hypertension, cardiac insufficiency, and rhythm disorders, respiratory disorders (asthma, rhinitis, cough, bronchitis, allergies, hypersensitivity), disorders of the gastrointestinal system such as esophageal ulcer, colitis, stress-related disorders, irritable bowel syndrome (IBS), inflammatory bowel diseases (IBD), acidic secretion, disorders of the urinary system (incontinence, neurogenic bladder), diseases of the immune system (rheumatoid arthritis), and more generally any neurokinin B-dependent pathology).

The appropriate single-dose forms for administration preferably comprise oral forms, such as tablets, optionally divisible tablets, gelatin capsules, powders and granules (for which the dosage unit can be represented, for example, by a sachet), and forms for sublingual and buccal administration, it also being possible for the forms for transdermal administration to be prepared by using the novel crystalline forms of the invention as active principles.

When a solid composition is prepared in the form of tablets, the active principle is mixed with a pharmaceutical excipient, such as gelatin, starch, lactose, magnesium stearate, talc or gum arabic. The tablets can be coated with sucrose or with other appropriate materials or they can be treated so that they have a prolonged or delayed activity and that they continuously release a predetermined amount of active principle.

A gelatin capsule preparation is obtained by mixing the active principle with a diluent and by pouring the mixture thus prepared into soft or hard gelatin capsules.

The active principle can also be formulated in the form of microcapsules, optionally with one or more fillers or additives.

In the aerosol forms, the active principle is administered by devices which make possible the absorption by the respiratory route of a dosage unit.

In the pharmaceutical compositions according to the present invention, the active principle can also be in the form of an inclusion complex in cyclo-dextrins, their ethers and their esters.

Finally, the active principle can be used in combination with other active principles, for example bronchodilators, antitussives or antihistamines.

The following EXAMPLES illustrate the invention.

EXAMPLE 1

(a) Osanetant Benzenesulfonate Solvate with 0.25 Mol of 4-methyl-2-pentanone.

A suspension of 1.424 kg of osanetant hydrochloride, obtained according to patent application EP-A-673 928, in 2.5 liters of water and 8.64 liters of 4-methyl-2-pentanone is prepared and 0.32 kg of 30% NaOH solution is added. The mixture thus obtained is heated at 80–85° C. with stirring for 15 minutes, the aqueous phase is then removed and the organic phase is washed until the pH becomes less than 8. The drying is carried out azeotropically and the solution is cooled to 25° C., and then a solution of 0.36 kg of benzenesulfonic acid in 1.15 l of 4-methyl-2-pentanone is added with stirring. After stirring for 15 hours, the osanetant benzenesulfonate, solvated with 0.25 mol of 4-methyl-2-pentanone, is filtered off; M.p.=176–177° C. (DSC); Yield: 94.8%.

(b) Osanetant 0.3 kg of a 30% sodium hydroxide solution is added to a mixture of 1.64 kg of the product obtained in stage (a), of 4.92 l of dichloromethane and of 3.28 l of water while maintaining the temperature at approximately 20° C., separating by settling is then carried out and the aqueous phase is extracted with dichloromethane. The combined organic phases are washed with water to a pH of less than 7.5 and then they are dried and concentrated by distilling off the dichloromethane/water azeotrope.

1.4 l of ethanol are added to the concentrated solution thus obtained and then the dichloromethane/ethanol azeotrope is removed while keeping the volume of the solution constant by addition of ethanol. 1 260 g of osanetant are obtained in solution in ethanol.

EXAMPLE 2

Osanetant-Crystalline Form I.

The procedures carried out as described in EXAMPLE 1 and the ethanolic solution obtained, composed of 3.3 kg of solution comprising osanetant in ethanol, is diluted with 1.76 kg of ethanol and then heated to 70° C. 3.2 l of water are gradually added at this temperature and the mixture is slowly cooled to 20–25° C. with vigorous stirring. As soon as the first crystals appear, stirring is continued for 15 hours and then the mixture is heated to 45–50° C. and is left at this temperature for 3 hours. The mixture is cooled to 0° C. and left at this temperature for 15 hours. The precipitate is filtered off, washed with a 60/40 (v/v) ethanol/water mixture cooled beforehand to 0° C. and dried under vacuum at 80° C.

Under these conditions, osanetant-crystalline form I was consequently obtained with an HPLC purity of 99.9% and with a yield of 90% in stage (b).

The osanetant-crystalline form I obtained in this preparation exhibited, by differential scanning calorimetry (DSC),
 a melting temperature of 143.6° C.
 an enthalpy of fusion of 68.5 J/g.

The osanetant-crystalline form I obtained in this preparation exhibits, by powder X-ray diffraction analysis with a SIEMENS D 500 TT diffractometer under the conditions given above, characteristic lines for the Bragg 2θ angles of 17.81°, 11.04° and 16.84°.

The relative diffractogram is recorded in FIG. 1.

The powder X-ray diffraction profile (diffraction angles) of the osanetant-crystalline form I from this preparation is given by the significant lines collated in TABLE 1 with the relative intensity, expresses percentage with respect to the most intense line.

TABLE 1

OSANETANT - CRYSTALLINE FORM I

| Diffraction bands (Bragg 2θ angles) | Relative intensity |
|---|---|
| 17.81 | 100 |
| 11.04 | 77.0 |
| 16.84 | 65.8 |
| 6.75 | 58.3 |
| 13.53 | 44.5 |
| 19.92 | 37.4 |
| 22.31 | 36.4 |
| 18.19 | 34.9 |
| 22.73 | 30.6 |
| 19.60 | 29.45 |
| 22.15 | 28.2 |
| 25.10 | 23.3 |
| 23.49 | 22.1 |
| 18.66 | 22.1 |
| 15.14 | 20.4 |

EXAMPLE 3

Osanetant-Crystalline Form II.

The mixture of 100 g of osanetant-crystalline form I, of 92 ml of ethanol and of 92 ml of isopropyl ether is heated at reflux under a nitrogen atmosphere and with stirring, and then 2.96 g of water and 306 ml of isopropyl ether are added.

The solution is filtered to remove any traces of interfering seeds, then it is cooled to 43–47° C. with stirring and is maintained at this temperature for 5–6 hours. Under these conditions, osanetant-crystalline form II crystallizes. Cooling is then carried out to approximately 25° C. and the mixture is kept stirred for 3 hours. The crystals, thus separated, are filtered, are washed with 100 ml of a 19/81 (v/v) ethanol/isopropanol ether mixture and are dried under vacuum at 65° C.

In a preparation under these conditions, 73 g of osanetant-crystalline form II were obtained with an HPLC purity of 99.9%.

The osanetant-crystalline form II obtained in this preparation exhibited, by differential scanning calorimetry (DSC):

a melting temperature of 141.8° C.

an enthalpy of fusion of 65.0 J/g.

The osanetant-crystalline form II obtained in this preparation exhibits, by powder X-ray diffraction analysis with a SIEMENS D 500 TT diffractometer under the conditions given above, characteristic lines for the Bragg 2θ angles of 18.35°, 18.58° and 18.97°.

Figure 2:
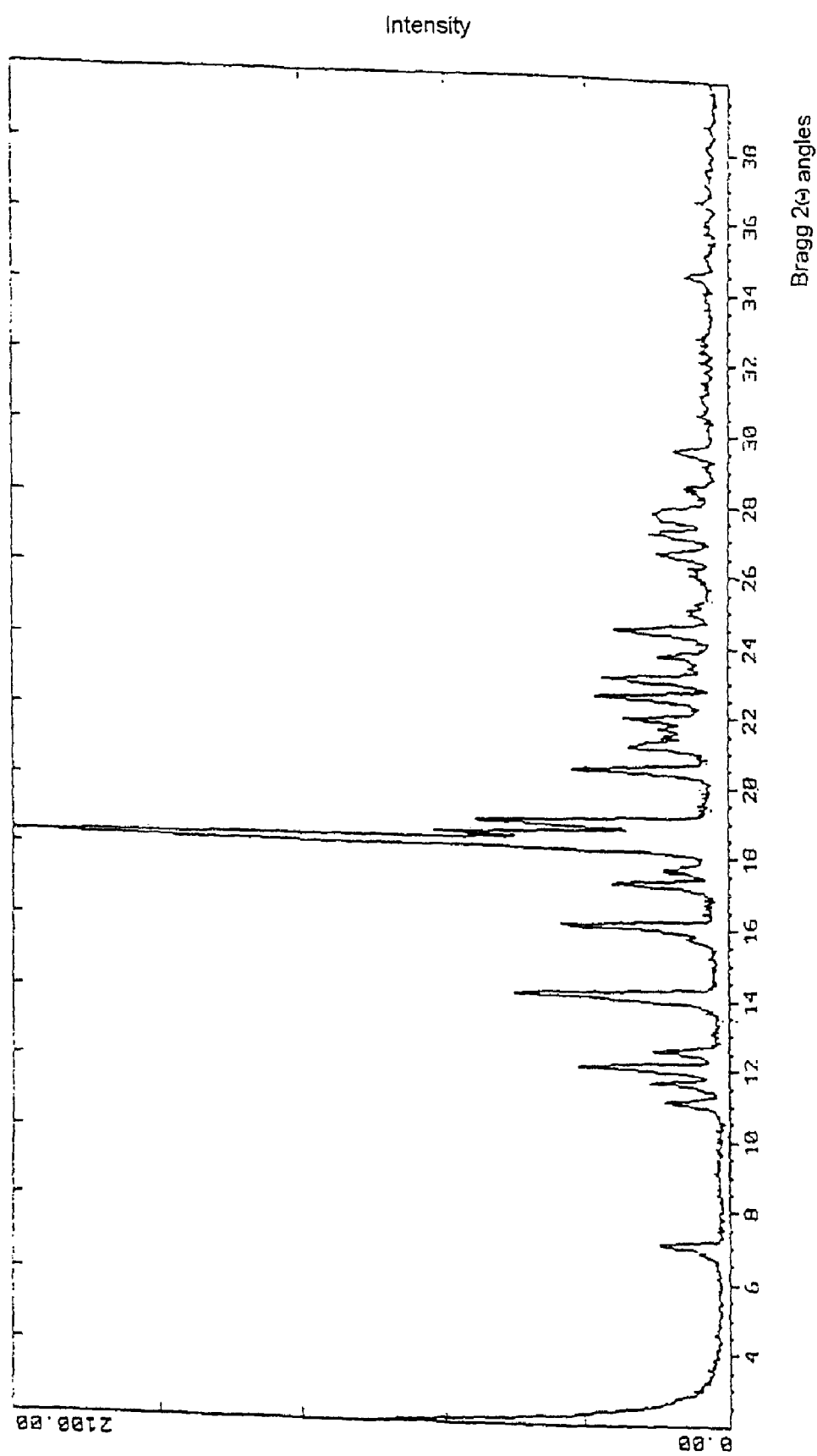

The relative diffractogram is recorded in FIG. 2.

The powder X-ray diffraction profile (diffraction angles) of the osanetant-crystalline form II from this preparation is given by the significant lines collated in TABLE 2 with the relative intensity, expressed as a percentage with respect to the most intense line.

TABLE 2

OSANETANT - CRYSTALLINE FORM II

| Diffraction bands (Bragg 2θ angles) | Relative intensity |
| --- | --- |
| 18.35 | 100 |
| 18.58 | 39.30 |
| 18.97 | 35.49 |
| 14.09 | 30.2 |
| 16.05 | 23.49 |
| 20.47 | 21.87 |
| 12.05 | 21.2 |
| 22.54 | 18.48 |
| 23.06 | 17.53 |
| 17.21 | 16.01 |
| 24.44 | 15.63 |
| 21.94 | 14.34 |
| 21.17 | 13.53 |
| 11.6 | 10.86 |
| 27.17 | 10.81 |

EXAMPLE 4

Osanetant Crystalline Form II.

The procedure is carried out as described in EXAMPLE 1 but the ethanolic solution obtained at the end of stage (b), composed of 3.3 kg of solution comprising osanetant in ethanol, is concentrated to 2.2 kg and then diluted with 1.175 l of isopropyl ether, heating is then carried out to reflux with stirring, and 37.9 ml of water and 3.9 l of isopropyl ether are added to the mixture. The solution thus obtained is filtered and is cooled to 450° C. with stirring, the crystallization is initiated and this temperature is maintained for 5 hours and 30 minutes. The mixture is cooled to 25° C. and kept stirred at this temperature for 3 hours. The product thus crystallized is filtered off, is washed with a 19/81 (v/v) ethanol/isopropyl ether mixture and is dried under vacuum at 65° C. to constant weight. Osanetant-crystalline form II is thus obtained.

EXAMPLE 5

Osanetant-Crystalline Form I 252 ml of water are gradually added to a solution, heated to 70° C., of 100 g of osanetant-crystalline form II (obtained as described in EXAMPLE 3) in 378 ml of ethanol, cooling is then slowly carried out to 20–25° C. with vigorous stirring, the crystallization is initiated and the mixture is kept stirred for 15 hours. The mixture is gradually heated to 45–50° C. and is left at this temperature for 3 hours. Slow cooling to 0° C. is carried out, this temperature is maintained for 15 hours and then the product thus precipitated is filtered off, washed with a 60/40 (v/v) ethanol/water mixture cooled beforehand to 0° C. and is dried under vacuum at 80° C. Osanetant-crystalline form I is thus obtained.

EXAMPLE 6

Osanetant-Crystalline Form I.

The procedure is carried out as described in EXAMPLE 1, stage a) and the first part of stage b)

After distilling off the dichloromethane/water azeotrope, isopropanol is added and then the dichloromethane/isopropanol azeotrope is removed while keeping the volume constant by addition of isopropanol. The isopropanol solution thus obtained is concentrated by distillation under reduced pressure until comprising 225.4 g of osanetant in 680 ml, i.e. a concentration of 260 g of osanetant/liter. This solution, the temperature of which is in the region of 60° C., is stirred at 400 revolutions/minutes with an impeller-type paddle stirrer with a rotation diameter of 7 cm for a reaction volume of 0.5 liter in a 2 liter reactor. Simultaneously, this solution is cooled with a linear cooling gradient of −20° C./hour. At the temperature of 40° C., the medium is seeded with 5% by weight of crystals of osanetant-form I and cooling of the solution obtained is continued to 0° C. with the cooling gradient of −20° C./hour. The medium is maintained at 0° C. for 6 hours and then the crystals formed are filtered off. They are washed with isopropanol and are then dried under vacuum at 80° C. Osanetant-crystalline form I is thus obtained with a yield of 93%.

EXAMPLE 7

Osanetant-Crystalline Form I 1.2 g of NaOH in 20 ml of 100% ethanol are added to a suspension of 20 g of osanetant benzenesulfonate, solvate with 0.25 mol of 4-methyl-2-pentanone, obtained in EXAMPLE 1, stage a), in 60 ml of 100% ethanol. After stirring for one hour at ambient temperature, the sodium benzenesulfonate formed is filtered off and washed with 10 ml of 100% ethanol. 50 ml of ethanol are distilled off at atmospheric pressure, 40 ml of water are then added at 70° C. and the mixture is allowed to return to ambient temperature. As soon as the first crystals appear, the mixture is stirred for 15 hours and is then heated at 45–50° C. for 3 hours. The mixture is cooled to 0° C. and this temperature is maintained for 15 hours. The precipitate formed is filtered off and washed with an ethanol/water (1/1, v/v) mixture cooled beforehand to 0° C. After drying under vacuum at 80° C., 15.14 g of osanetant-form I are obtained (yield 99.6%).

EXAMPLE 8

Osanetant-Crystalline Form I

The procedure is carried out as described in EXAMPLE 1, stage a) and the first part of stage b)

After distilling off the dichloromethane/water azeotrope, ethanol is added and then the dichloromethane/ethanol azeotrope is removed while keeping the volume constant by addition of ethanol. The ethanol solution thus obtained is concentrated by distillation until comprising 100 g of osanetant in 240 ml of ethanol, i.e. a concentration of osanetant of 34.7% by weight. This solution, the temperature of which is in the region of 70° C., is diluted with 160 ml of water, i.e. a final concentration of osanetant of 22.3% by weight. This solution, stirred with an impeller-type paddle stirrer, is cooled with a linear cooling gradient of −15° C./hour. At the temperature of 40° C., the medium is seeded with 5% by weight of crystals of osanetant (form I) and cooling is continued with a cooling gradient of −5° C./hour to 20° C. The medium is maintained at 20° C. for 4 hours. The osanetant suspension thus obtained is reheated with a heating gradient of +14° C./hour to 48° C. and then maintained at 48° C. for 2 hours. This suspension is cooled to 20° C. with a cooling gradient of −5° C./hour. The suspension is maintained at 20° C. for 4 hours and then the crystals formed are filtered off. They are washed with the ethanol/water (60/40, v/v) mixture and are then dried under vacuum at 80° C. Osanetant-crystalline form I is thus obtained with a yield of greater than 90%.

The invention claimed is:

1. A process for the crystallization of osanetant wherein: osanetant is crystallized from an ethanol/water mixture by heating a solution of osanetant in ethanol/water mixture to a temperature of less than or equal to the reflux temperature of the solvent and then cooling to obtain crystalline form I of osanetant; or heating a solution of osanetant in isopropanol to a temperature of less than or equal to the reflux temperature of the solvent and then cooling to give the crystalline form I.

2. A process for the preparation of osanetant wherein: osanetant is crystallized from an ethanol/isopropyl ether/water mixture by adding isopropyl ether and water to a solution of osanetant in ethanol and heating to a temperature of less than or equal to the reflux temperature of the solvent and then cooling to give the crystalline form II of osanetant.

3. A process according to claim 1 wherein: either water is added to a solution of osanetant in ethanol and heating is carried out to a temperature of less than the reflux temperature of the solvent and then cooling is carried out in order to obtain osanetant-crystalline form I;
or a solution of osanetant in isopropanol is heated to a temperature of less than the reflux temperature of the solvent and cooling is carried out in order to obtain osanetant-crystalline form I.

4. A process according to claim 3 for the preparation of osanetant-crystalline form I wherein: either water is added to a solution of osanetant in ethanol and heating is carried out to a temperature of 60° C. to 75° C. and then cooling is carried out; or a solution of osanetant in isopropanol is heated to 60° C.–80° C. and cooling is carried out.

5. A process according to claim 4 wherein water is added to a solution of osanetant in ethanol, heating is carried out to a temperature of 60 to 75° C. and then cooling is carried out.

6. A process according to claim 5 wherein cooling is carried out to 20–25° C., then either the crystallization is initiated or there is a wait for the first crystals to appear, and, subsequently, the temperature is increased to 45–50° C., cooling is then carried out to 0° C. and this temperature is maintained.

7. A process according to claim 5 wherein cooling is carried out to a temperature in the region of 40° C., the crystallization is initiated, cooling is continued to 20–25° C., the osanetant suspension formed is reheated to 45–50° C. and then cooling is carried out to 20–25° C.

8. A process according to claim 4 wherein a solution of osanetant in isopropanol is heated to a temperature of 60–80° C. and then cooling is carried out.

9. A process according to claim 8 wherein cooling is carried out to a temperature of between 0 and 50° C., the crystallization is then initiated, cooling is subsequently carried out to 0° C. and the mixture is maintained at 0° C.

10. A process according to claim 2 for the preparation of osanetant-crystalline form II wherein isopropyl ether and water are added to a solution of osanetant in ethanol, heating is carried out to reflux and then cooling is carried out.

11. A process according to claim 10 wherein a solution of osanetant in an ethanol/isopropyl ether mixture is heated to reflux, isopropyl ether and water are added, cooling to 40–50° C. is allowed to take place, then either the crystallization is initiated or there is a wait for the first crystals to appear, and cooling is subsequently carried out to 20–25° C.

12. A process according to claim 1 wherein the osanetant to be crystallized is prepared by neutralization of its benzenesulfonate.

13. Osanetant-crystalline form I, wherein it exhibits:
a melting temperature with a peak with a maximum at 143.6±0.5° C.
an enthalpy of fusion of 68.5±0.5 J/g; and
wherein its powder X-ray diffractogram exhibits characteristic Bragg 2θ lines at approximately 17.81°, 11.04° and 16.84°.

14. Osanetant-crystalline form II, wherein it exhibits:
a melting temperature with a peak with a maximum at 141.8±0.5° C.
an enthalpy of fusion of 65.0±0.5 J/g; and
wherein its powder X-ray diffractogram exhibits characteristic Bragg 2θ lines at approximately 18.35°, 18.58° and 18.97°.

15. Osanetant-crystalline form I according to claim 13, wherein it exhibits:
a melting temperature with a peak with a maximum at 143.6±0.5° C.
an enthalpy of fusion of 68.5±0.5 J/g.

16. Osanetant-crystalline form I according to claim 13, wherein its powder X-ray diffractogram exhibits characteristic Bragg 2θ lines at approximately 17.81°, 11.04° and 16.84°.

17. Osanetant-crystalline form II according to claim 14, wherein it exhibits:
a melting temperature with a peak with a maximum at 143.8±0.5° C.
an enthalpy of fusion of 65.0±0.5 J/g.

18. Osanetant-crystalline form II according to claim 14 wherein its powder X-ray diffractogram exhibits characteristic Bragg 2θ lines at approximately 18.35°, 18.58° and 18.97°.

* * * * *